United States Patent [19]

Jarque et al.

[11] 4,172,201

[45] Oct. 23, 1979

[54] ALPHA-2,5,9-TRIMETHYL-BENZO(b)-THIENE(2,3,-f)MORPHAN AND PRECURSOR THEREOF

[75] Inventors: Ricardo G. Jarque, Barcelona; Mercedes A. Domingo, San Juan Despi; Juan B. Cartes, Barcelona; Cristóbal M. Roldán; Fernando R. Peinado, both of Madrid, all of Spain

[73] Assignee: Laboratorios Made, S.A., Madrid, Spain

[21] Appl. No.: 874,608

[22] Filed: Feb. 2, 1978

[30] Foreign Application Priority Data

Feb. 25, 1977 [ES] Spain .................................. 456280

[51] Int. Cl.² ................... C07D 495/08; C07D 409/06
[52] U.S. Cl. ........................................ 546/63; 424/263; 424/267; 546/274; 549/49

[58] Field of Search ................ 260/DIG. 13, 293.54, 260/294.8 C; 424/263, 267; 546/63, 274

[56] References Cited

U.S. PATENT DOCUMENTS 3,382,249  5/1968  Albertson .................. 260/293.54

OTHER PUBLICATIONS

Montzka, T. et al., *J. Het. Chem.*, 11, 853–855 (1974).
Perry, R. et al., *J. Med. Chem.*, 10, 1184–1186 (1967).

*Primary Examiner*—John M. Ford
*Assistant Examiner*—Richard A. Schwartz
*Attorney, Agent, or Firm*—Ladas, Parry, Von Gehr, Goldsmith & Deschamps

[57] ABSTRACT

Alpha-2,5,9-trimethyl-benzo [b]thiene [2,3-f]morphan and 2-(3-benzo[b]thienylmethyl)-1,3,4-trimethyl-1,2,5,6-tetrahydropyridine or their pharmacologically acceptable acid addition salts are useful as analgesic agents.

3 Claims, No Drawings

ALPHA-2,5,9-TRIMETHYL-BENZO(b)THIENE(2,3-f)MORPHAN AND PRECURSOR THEREOF

This invention relates to obtaining α-2,5,9-trimethyl-benzo[b]thiene[2,3-f]morphan (I), an intermediate from its preparation, 2-(3-benzo[b]thienylmethyl)-1,3,4-trimethyl-1,2,5,6-tetrahydropyridine (II) and the addition salts thereof with pharmacologically acceptable acids, for example hydrochlorides.

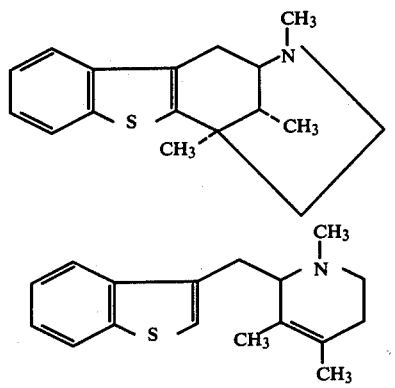

The cited compounds are new substances of interest as analgesics, and are prepared according to the following reaction sequence:

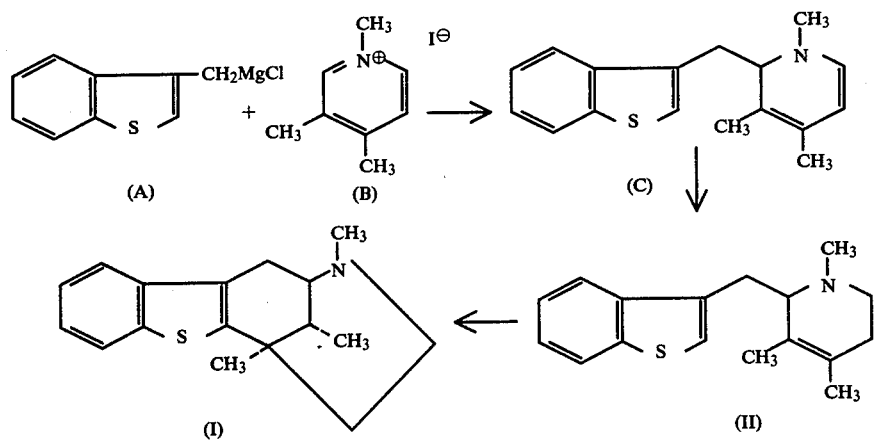

In the first part of the process, 3-chloromethyl-benzo[b]thiophene magnesiane) (A) is obtained in conditions of high dilution and in an inert atmosphere, and is made to react at reflux temperature with 1,3,4-trimethyl-pyridinium iodide (B) in anhydrous ether, thereby producing the unstable 2-(3-benzo-[b]thienylmethyl)-1,3,4-trimethyl-1,2-dihydropyridine intermediate. Said intermediate, without subsequent purification, is reduced in basic medium with sodium borohydride in aqueous methanolic solution. The organic layer provides a mixture from which isolation can be made, by distillation, of the compound (II) 2-(3-benzo[b]thienylmethyl)-1,3,4-trimethyl-1,2,5,6-tetrahydro-pyridine, from which the corresponding hydrochloride is obtained. In a following step of the process the previously obtained raw mixture is heated at 135° C. for 12 hours in a strong acid such as, for example, 48% aqueous hydrobromic acid. It is poured over ice and water, alkalinized with ammonium hydroxide and extracted with ether, thus producing the α-2,5,9-trimethylbenzo[b]thiene[2,3-f]-morphan (I).

The following examples are given only as illustrations, and must not be considered in any way limitative of the scope of the invention.

EXAMPLE 1

Obtaining 2-(3-benzo[b]thienylmethyl)-1,3,4-trimethyl-1,2,5,6-tetrahydropyridine To obtain 3-benzo[b]thienylmethylmagnesium chloride, use is made of the "modified cyclic reactor" embodying a continuous flow column provided with a separation funnel, coolant and reaction flask. The reactor column is packed with 70 g of magnesium in chips alternated with thin layers of mercuric chloride, and is covered with a saturated solution of mercuric chloride in anhydrous ether. Following 48 hours of repose, 250 ml of anhydrous ether are introduced in the flask and are made to reflux for 2 hours. The flask is substituted by another equipped for mechanical stirring in which 13.6 g of 1,3,4-trimethylpyridinium iodide are introduced in suspension with 300 ml of anhydrous ether. 10.6 g of 3-chloromethyl-benzo[b]thiophene dissolved in 150 ml of anhydrous ether are placed in a separation funnel. Some ml of the halogenide solution are added to the magnesium column, and when it is observed that the reaction has begun the flask is heated to reflux temperature, with the addition continuing slowly for 3 hours. During the entire process a nitrogen atmosphere is maintained in the system.

When the addition is concluded, reflux is continued for 4 hours, the ether solution is poured over 250 ml of aqueous solution of ammonium chloride and ice, the mixture is alkalinized with concentrated ammonium hydroxide and is extracted with ether. The ether solution is extracted with 10% hydrochloric acid, the aqueous layer is alkalinized with concentrated ammonium hydroxide and is extracted with ether. The ether extract dried with magnesium sulfate and evaporated provides 8.3 g of the unstable 2-(3-benzo[b]thienylmethyl)-1,3,4-trimethyl-1,2-dihydropyridine intermediate. To the 8.3 g of said intermediate dissolved in 45 ml of methanol are added 25 ml of 1N sodium hydroxide and 2 g of sodium borohydride. The mixture is heated to reflux temperature and is stirred for 12 hours. The resulting product is extracted with ether and is dried with magnesium sulfate. Once the ether has evaporated, 6.36 g of reaction mixture are obtained. The global yield of the process is 40%. From said mixture the 2-(3-benzo[b]thienylmethyl)-1,3,4-trimethyl-1,2,5,6-tetrahydropyridine (II) can be isolated by distillation (b.p. 104–130/0.07 mm Hg) followed by recrystallizaton of the corresponding hydrochloride. A sample recrystallized from ether-acetone has a melting point of 185°–190° C.

Calculated analysis for $C_{17}H_{22}Cl\ SN$: Calculated: C=66.32%; H=7.19%; N=4.54%; S=10.41%; Cl=11.51%. Found: C=66.29%; H=7.59%; N=4.36%; S=10.39%; Cl=11.36%.

EXAMPLE 2

Obtaining α-2,5,9-trimethyl-benzo[b]thiene[2,3-f]morphan

A solution of 4.8 g of the tetrahydropyridine previously obtained in 55 ml of 48% aqueous hydrobromic acid is heated at 130°–5° C. for 12 hours. The mixture is allowed to cool, is poured over ice and water, alkalinized with ammonium hydroxide and is extracted with ether. The ether extract, dried with magnesium sulfate and evaporated, provides 3.9 g of an oil purified by distillation, the distilling fraction collecting between 107°–190° C./0.07 mm Hg.

Yield is 68%. From this fraction the α-2,5,9-trimethyl-benzo[b]thiene[2,3-f]morphan is separated by precipitation of its hydrochloride which is purified by recrystallization from ether-acetone obtaining a solid of a melting point of 135°–137° C.

Calculated analysis for $C_{17}H_{22}Cl\ N\ S.\ H_2O$: C, 62.69; H 7.36; N 4.29; S 9.84; Cl 10.88. Found % C, 62.64; H 7.23; N 4.02; S 9.64; Cl 10.86.

PHARMACOLOGY OF THE PRODUCTS OF THE INVENTION PRODUCTS

I—α-2,5,9-trimethyl-benzo[b]thiene[2,3-f]morphan.
II—2-(3-benzo[b]thienylmethyl)-1,3,4-trimethyl-1,2,5,6-tetrahydropyridine.

These are products of analgesic activity. Their activity has been studied in comparison with that of dextropropoxyphene.

A.—Acute Toxicity

Studies of acute toxicity have been made in I.C.R. Swiss albino mice of 20±2 g weight, of both sexes. The products have been administered intraperitoneally (i.p.). Acute toxicity calculations have been made by the Litchfield-Wilcoxon method.

TABLE 1

| Products | Lethal Dose 50 ($LD_{50}$) | |
| --- | --- | --- |
| I | 76.4 | mg/kg |
| II | 127.3 | " |
| Dextropropoxyphene | 140 | " |

B.—Analgesic Activity

1. Thermal analgesia

The thermal analgesic effect has been studied in I.C.R. Swiss albino mice. The 55° C. "hot plate" technique has been used. Batches of 10 mice were made.

The products under study have been administered i.p. After 30 minutes the mice were placed on the hot plate and note was taken, in seconds, of the time it took them to jump. Batches have been made of control animals injected only with distilled water.

The results are given in Tables 2 and 3:

TABLE 2

| Treatment | Dose | Jumping Time in sec. $\bar{x} \pm$ S.E.M. | Significance of Diff. Dextroprop. | Control |
| --- | --- | --- | --- | --- |
| Control | — | 64 ± 7.919 | — | — |
| Prod. I | 50mg/kg | 142.4 ± 12.245 | N.S. | $p < 0.00005$ |
| Dextropropoxyphene | 50mg/kg | 164 ± 7.319 | — | $p < 0.00005$ |

The analgesic activity of product I is not significantly different from that of dextropropoxyphene, using the same dose.

TABLE 3

| Treatment | Dose | Jumping time in sec. $\bar{x} \pm$ S.E.M. | Significance of Diff. Dextroprop. | Control |
| --- | --- | --- | --- | --- |
| Control | — | 38 ± 4.253 | — | — |
| Prod. II | 30mg/kg | 78.6 ± 11.041 | N.S. | $p < 0.005$ |
| Dextropropoxyphene | 30mg/kg | 83.7 ± 12.267 | — | $p < 0.005$ |

The analgesic activity of product II is not significantly different from that of dextropropoxyphene, using the same dose.

2. Chemical analgesia

The analgesic effect has been studied in I.C.R. Swiss albino mice, employing the acetic acid writhing technique. Batches of 10 mice were made.

The products studied have been administered i.p., and after 30 minutes the mice have been injected intraperitoneally with 0.25 ml of 1% acetic acid. A batch of control animals have received only the acetic acid. For 20 minutes following the injection of the acetic acid the number of writhes is noted in each mouse. The results are shown in Tables 4 and 5.

TABLE 4

| Treatment | Dose | No. of writhes $\bar{x} \pm$ S.E.M. | Significance of Diff. Dextroprop. | Control |
| --- | --- | --- | --- | --- |
| Control | — | 100.5 ± 13.633 | — | — |
| Prod. I | 25mg/kg | 53.1 ± 16.895 | N.S. | $p < 0.05$ |
| Dextropropoxyphene | 25mg/kg | 47.444 ± 7.151 | — | $p < 0.005$ |

The analgesic activity of product I is not significantly different from that of dextropropoxyphene, using the same dose.

TABLE 5

| Treatment | Dose | No. of writhes $\bar{x} \pm$ S.E.M. | Significance of Diff. Dextroprop. | Control |
|---|---|---|---|---|
| Control | — | 112.43 ± 3.24 | — | — |
| Prod. II | 30mg/kg | 55.75 ± 7.99 | $p < 0.05$ | $p < 0.0005$ |
| Dextropropoxyphene | 30mg/kg | 31.77 ± 5.8 | — | $p < 0.00005$ |

Product II has analgesic activity, but of lesser potency than that of the dextropropoxyphene.

What is claimed:

1. Alpha-2,5,9-trimethyl-benzo[b]thiene[2,3-f] morphan or 2-(3-benzo[b]thienylmethyl)-1,3,4-trimethyl-1,2,5,6-tetrahydropyridine or one of their pharmacologically acceptable acid addition salts.

2. The compound defined in claim 1 which is alpha-2,5,9-trimethylbenzo[b]thiene[2,3-f]morphan of the formula:

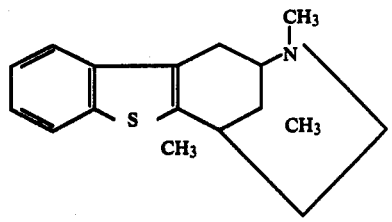

or a pharmacologically acceptable acid addition salt thereof.

3. The compound defined in claim 1 which is 2-(3-benzo[b]thienylmethyl)-1,3,4-trimethyl-1,2,5,6-tetrahydropyridine of the formula:

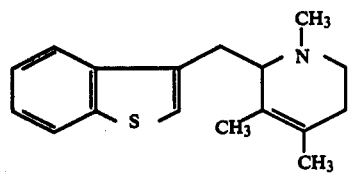

or a pharmacologically acceptable acid addition salt thereof.

* * * * *